United States Patent [19]
Almon

[11] Patent Number: 5,354,438
[45] Date of Patent: Oct. 11, 1994

[54] SEPARATION OF METAL IONS FROM AQUEOUS SOLUTIONS

[75] Inventor: Amy C. Almon, Augusta, Ga.

[73] Assignee: United States Department of Energy, Washington, D.C.

[21] Appl. No.: 72,408

[22] Filed: Jun. 7, 1993

Related U.S. Application Data

[62] Division of Ser. No. 798,779, Nov. 27, 1991, abandoned.

[51] Int. Cl.⁵ .................... G01N 27/26; C25F 1/00
[52] U.S. Cl. .................... 204/140; 204/141.5; 204/149; 204/409; 204/434; 204/153.1
[58] Field of Search ........... 204/153.1, 105 R, 140, 204/141.5, 149, 434, 409

[56] References Cited

U.S. PATENT DOCUMENTS

| | | | |
|---|---|---|---|
| 4,058,446 | 11/1977 | Zirino et al. | 204/434 |
| 4,146,436 | 3/1979 | Kellermann et al. | 204/153.1 |
| 4,776,932 | 10/1988 | Grossman et al. | 204/105 R |
| 4,861,555 | 8/1989 | Mowery, Jr. | 204/149 |

*Primary Examiner*—John Niebling
*Assistant Examiner*—Bruce F. Bell
*Attorney, Agent, or Firm*—Brian R. Tumm; Harold M. Dixon; William R. Moser

[57] ABSTRACT

A process and apparatus for quantitatively and selectively separating metal ions from mixtures thereof in aqueous solution. The apparatus includes, in combination, a horizontal electrochemical flow cell containing flow bulk electrolyte solution and an aqueous, metal ion-containing solution, the cell containing a metal mesh working electrode, a counter electrode positioned downstream from the working electrode, an independent variable power supply/potentiostat positioned outside of the flow cell and connected to the electrodes, and optionally a detector such as a chromatographic detector, positioned outside the flow cell. This apparatus and its operation has significant application where trace amounts of metal ions are to be separated.

16 Claims, 1 Drawing Sheet

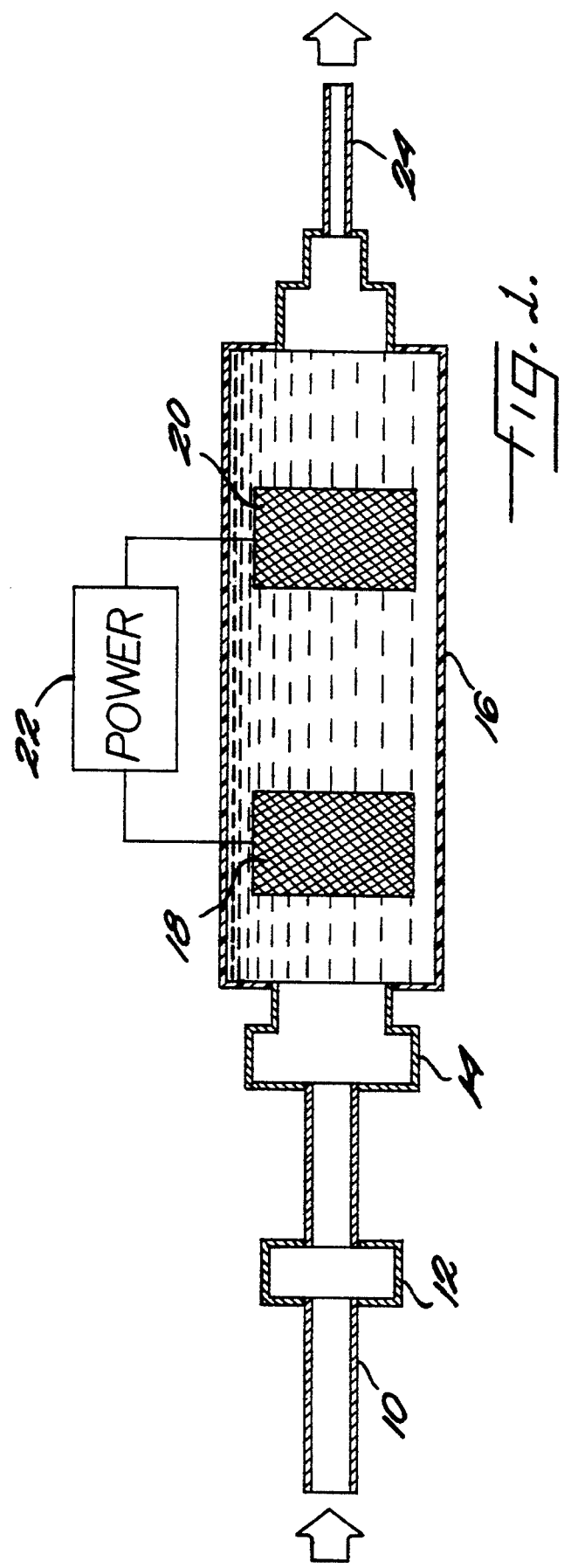

SEPARATION OF METAL IONS FROM AQUEOUS SOLUTIONS

This application is a divisional of Ser. No. 798,779, filed Nov. 27, 1991 now abandoned.

BACKGROUND OF THE INVENTION

1. Field of the Invention

The present invention relates to the separation of metal ions in aqueous solutions. More specifically, the present invention relates to an electrocell and method for using the electrocell to separate trace ions from aqueous solutions. The United States Government has fights in this invention pursuant to Contract No. DE-AC09-89SR18035 between the U.S. Department of Energy and Westinghouse Savannah River Company.

2. Discussion of Background

There has been a need for a viable and relatively simple method and apparatus to separate trace metals from solutions thereof quantitatively. Solutions containing such metals range from seawaters to drinking water and other solutions that may contain metal ions.

Several known systems and techniques for performing trace metal analyses to indicate the presence and concentration of metals of interest are found in U.S. Pat. No. 3,904,487, U.S. Pat. No. 4,829,007, and U.S. Pat. No. 4,058,446. These systems, including the apparatus utilized in each, function according to their respective disclosures to achieve the results specified.

U.S. Pat. No. 4,058,446 discloses an improvement for an anodic stripping voltammetry system (ASV) for the measurement of concentration and presence of trace metals in seawater. In this disclosure, a combination electrode is made from a porous polyethylene cylinder having a coaxial base for receiving the following solution. A helically extending silver/silver chloride reference electrode is disposed on the outside of the cylinder and a platinum counter electrode is located in its bore. The porous polyethylene prevents chlorides from contaminating the reference electrode while the counter electrode drains off current.

U.S. Pat. No. 4,829,007 is directed to a process for detecting trace amounts of plateable metal in an aqueous fluid such as drinking water or industrial effluents. The pH of the fluid being treated is adjusted to the desired value. In a first electrochemical cell, the metal in the fluid is deposited upon a glassy carbon plating electrode held at a negative potential. The carbon electrode is de-plated in a second electrochemical cell. A porous solid test matrix impregnated with electrolyte is maintained proximate to the de-plating electrode (anode) and the cathode for retaining in solution the resulting metal ions formed from the de-plated metal. Upon completion of the de-plating step, a color indicator is added to the test matrix to provide an indication of the presence of the metal. Levels of lead as low as 5 ppb can be detected.

U.S. Pat. No. 3,904,487 discloses an apparatus and method of determining the presence and concentration of trace metals in seawater; anodic stripping voltammetry (ASV) method and apparatus are utilized. A tubular, mercury-graphite electrode is coupled to receive a flowing mercury solution; a thin film of mercury is deposited on the inner surface of this electrode after the plating potential is coupled. A solution of seawater containing trace metals is then pumped through this electrode and trace metals are reduced onto the activated mercury film on reconnecting of plating potential to the electrode. After a pre-determined time, a pulsed scanning potential gradient is applied across the two electrodes; individual types of trace metals are then selectively stripped (oxidized) and the magnitudes of the currents at these levels are monitored and are proportional to the concentration of the trace metals. The mercury film is then stripped away by increasing the scanning potential, a fresh film of mercury is then deposited and the electrode then is used on another sample solution containing trace metals.

SUMMARY OF THE INVENTION

According to its major aspects and broadly stated, the present invention is directed to a method of and apparatus for quantitatively and selectively separating, removing and identifying trace amounts of metal ions in aqueous solutions containing said ions. The metal ions processed in the practice of this invention may be present as two or more in solution. If, for example, only two metal ions are to be separated, the follow-up identification step may not be required after separation and removal.

According to the present invention, metal ions present in mixtures of said ions in aqueous solution can be quantitatively and selectively separated from said solution; the effluent containing separated ions can be collected as fractions or sent off to subsequent detectors for identification.

Other features and advantages of the present invention will be apparent to those skilled in the art from a careful reading of the Detailed Description of a Preferred Embodiment presented below and accompanied by the drawing.

BRIEF DESCRIPTION OF THE DRAWINGS

In the drawings,

FIG. 1 sets forth a schematic representation of apparatus that quantitatively and selectively separates trace metal ions present in aqueous solution.

DETAILED DESCRIPTION OF A PREFERRED EMBODIMENT

The present invention provides a unique system, process and apparatus, for the quantitative recovery of metal ions, including trace amounts, from aqueous solutions containing the ions. These separated ions in their flowing effluent can be recovered as fractions or subjected to a follow-up identification procedure with use of, for example, a chromatographic detector.

In the practice of this invention, the metal ion-containing samples must be in an aqueous solution; if in an organic solution, the organic solution will coat the electrode surfaces.

Reference is made to FIG. 1 for a detailed apparatus that can be utilized in the practice of this invention.

FIG. 1 "10" is an inlet tube for a stream containing bulk electrolyte solution; this solution is introduced at a controlled flow rate. "12" is an injection port for the aqueous solution sample being processed; the sample volume will be controlled and flow at a rate that depends on the concentration of the metal ions to be processed.

"14" is a conventional screw fitting.

"16" is a horizontal flowing tube with an inner diameter of 0.5 cm and a length of 20.5 cm which can be made of "TEFLON" (a trademark of E. I. Dupont de Nemours & Company, Inc.), chemically resistant polymer or plastic; it contains electrodes "18" and "20".

"18" is a working electrode made of steel mesh, preferably stainless, onto which metal ions plate out.

"20" is an auxiliary or "counter" electrode preferably made stainless steel and preferably of the same size and consistency as working electrode "18".

"22" represents a variable power supply potentiostat that is standard and imposes the desired voltages on working electrode "18" and completes the circuit between working electrode "18" and auxiliary (counter) electrode "20".

"24" is an outlet tube containing the effluent from flow tube "16" and contains separated metal ions.

A horizontally flowing stream containing bulk electrolytic solution is introduced through inlet tubing; this solution functions to transport the sample and provide electric conductivity between the two electrodes positioned in sequence in the horizontal flowing tube. The aqueous solution sample containing trace amounts of metal ions to be separated is introduced into the flowing carrier stream through an injection port; the carrier stream flow rate can range between 0.2 ml/min. and 2.5 ml/min.; the sample volume can be between 100 $\mu$l and 100 ml. depending on the concentration of trace metals ions.

A nominal flow rate of 1 ml per minute is satisfactory. A conventional flowmeter is used for measurement of electrolyte flow rate. If the flow rate increases, the column pressure increases and the resulting peaks produced by the strip chart recorder are more spread out. If the flow rate decreases, the peaks become narrower but also more closely spaced and can blend together.

The flow tube dimensions, which are an inner diameter of 0.5 cm and a length of 20.5 cm, are not critical but are preferred; they could be 20% more or less, which are an inner diameter of 0.5 cm and a length of 20.5 cm. The flowing tube is preferably made of, for example, Teflon ® because of its inertness and low cost and because it is easily machined.

The strip chart recorder or integrator is preferably an Astrophysics 4400 Integrator manufactured by the Astrophysics Company.

Any liquid chromatograph having variable speed can be used, such as a Hewlett Packard, Waters Chromatography or Dionex gradient pump could be used.

The bulk electrolyte acts as a mobile flowing phase to carry the sample through the horizontal column. This electrolyte flows continuously through the column and maintains electrical contact between the electrodes. It must be used regardless of the composition of the metal ion sample in aqueous solution. Examples of electrolyte solutions that can be used include 0.1 m $KNO_3$, 0.1 m KCl and 0.1 NACl.

Stainless steel is the preferred electrode material because of cost. Platinum, pure or plate, would be better, however, because of its better electron exchange properties. If stainless steel is not the electrode material of choice for the electrodes, the time to strip off metal ions would change, however, the voltage range would not change.

The selection of counter electrode metal is not critical and does not have to be the same material as the working electrode. Its only function is to maintain a balance of charge in solution. Stainless steel is preferred simply because of cost and performance.

The variable power supply/potentiostat can be selected off the shelf. It can be PAR Model 173 or 386, manufactured by Princeton Applied Research; or, for example, BAS Model 100, 100A or 100B manufactured by Bio Analytical Systems.

Specific solutions containing specific trace metals and mixtures of said metals that can be processed in the practice of this invention include dissolved sludge, radioactive solutions, water samples, stream samples, pond cooling water samples and waste pond by-product samples.

Plutonium and uranium metal ion separation can be achieved as can metal ion mixtures of plutonium and neptunium. Other metal ion mixtures that can be processed include Cu, Au, Ag and Hg in reactor moderator water; silver and plutonium in separation samples in nitric acid and Cu, Al and Fe in waste water basin samples. A plurality of metal ions in aqueous solution can be separated.

It is understood that the herein described process and apparatus can be varied and modified yet remain within the spirit and scope of the appended claims, as it would be understood and practiced by one skilled in this field of technology.

What is claimed is:

1. The method of quantitatively and selectively separating metal ions present in mixtures of said ions in an aqueous ion-containing solution, said method comprising the steps of:
    passing said ion-containing solution at a controlled flow rate, into a flowing bulk electrolyte solution to form a combined solution;
    passing said combined solution through, in sequence, a working electrode and a counter electrode located downstream from said working electrode, said electrodes each having a working surface and each being connected to an independent variable power source of an electrical potential;
    maintaining said electrical potential initially at a negative value to reduce said metal ions onto said surface of said working electrode;
    increasing the potential of said working electrode linearly to selectively oxidize off the plated metal ions from said working surface of said working electrode as the oxidation potential of said plated metal ions is reached, thereby separating metal ions selectively;
    passing said separated metal ions away from said working electrode as effluent; and
    recovering said separated metal ions as fractions.

2. The method of claim 1, wherein said working electrode is in the form of a mesh.

3. The method of claim 1, wherein said working electrode is made of stainless steel mesh.

4. The method of claim 1, wherein said working electrode is made of stainless steel mesh and said counter electrode is made of stainless steel.

5. A method for separating metal ions from an aqueous solution, said method comprising the steps of:
    mixing said aqueous solution with a bulk electrolyte solution to form a combined solution;
    passing said combined solution through an electrocell, said electrocell having a working electrode and a counter electrode;
    reducing said metal ions contained in said combined solution onto said working electrode;
    selectively oxidizing said metal ions from said working electrode into said bulk electrolyte; and
    recovering said oxidized metal ions from said bulk electrolyte.

6. The method as recited in claim 5, wherein said working electrode has a working surface, and wherein said reducing step further comprises applying a negative electrical potential to said working electrode with respect to said counter electrode so that said metal ions contained in said combined solution reduce to said working surface of said working electrode.

7. The method as recited in claim 5, wherein said aqueous solution contains a plurality of species of metal ions each having an oxidation potential, and wherein said oxidizing step further comprises applying a linearly increasing electrical potential across said working and counter electrodes so that said metal ions are selectively oxidized off said working electrode as said electrical potential reaches said oxidation potential.

8. The method as recited in claim 5, wherein said working and counter electrodes are oriented perpendicular to the flow of said combined solution through said electrocell, and wherein said passing step further comprises passing said combined solution across, in sequence, said working electrode and said counter electrode.

9. The method as recited in claim 5, wherein said working electrode is in the form of a mesh, and wherein said passing step further comprises passing said combined solution through said working electrode.

10. The method as recited in claim 5, wherein said counter electrode is in the form of a mesh, and wherein said passing step further comprises passing said combined solution through said counter electrode.

11. The method as recited in claim 5, wherein said metal ions oxidized off said working electrode form a resulting solution in said electrocell, and wherein said recovering step further comprises removing said resulting solution from said electrocell as effluent and recovering said separated metal ions from said effluent as fractions.

12. The method as recited in claim 5, wherein said mixing step further comprises injecting said aqueous solution into said electrolyte solution as said electrolyte solution flows into said electrocell.

13. A method of quantitatively and selectively separating metal ions present in mixtures of said ions in an aqueous ion-containing solution, said method for use with an electrocell having an inlet tube with an injection port, a working electrode, a counter electrode and an outlet tube, said method comprising the steps of:

pumping at a known rate a bulk electrolyte solution into said electrocell through said inlet tube;

injecting said aqueous ion-containing solution into said bulk electrolyte solution prior to said electrolyte solution entering said electrocell, said aqueous ion-containing solution and said electrolyte solution forming a combined solution entering said electrocell;

passing said combined solution through said electrocell so that said combined solution passes, in sequence, said working electrode and said counter electrode, said electrodes each having a working surface;

applying a negative electrical potential to said working electrode with respect to said counter electrode so that said metal ions in said combined solution reduce onto said working surface of said working electrode;

increasing the electrical potential of said working electrode linearly with respect to said counter electrode to selectively oxidize said metal ions from said working surface of said working electrode, said oxidized metal ions forming a resulting solution within said electrocell;

removing said resulting solution of separated metal ions from said electrocell through said outlet tube, said resulting solution passing out of said electrocell as effluent; and recovering said separated metal ions from said effluent as fractions.

14. The method as recited in claim 13, wherein said aqueous ion-containing solution contains a plurality of species of metal ions each having an oxidation potential and a reduction potential, and wherein said increasing step further comprises applying a linearly increasing electrical potential across said working and counter electrodes so that said metal ions are selectively oxidized off said working electrode as said electrical potential reaches said oxidation potential.

15. The method as recited in claim 13, wherein said working and counter electrodes are oriented perpendicular to the direction of flow of said combined solution through said electrocell, and wherein said passing step further comprises passing said combined solution across, in sequence, said working electrode and said counter electrode.

16. The method as recited in claim 13, wherein each of said working electrode and said counter electrode is in the form of a mesh, and wherein said passing step further comprises passing said combined solution through, in sequence, said working electrode and said counter electrode.

* * * * *